United States Patent
Choi et al.

(10) Patent No.: US 9,833,376 B2
(45) Date of Patent: Dec. 5, 2017

(54) WALKING ASSISTANCE METHODS AND APPARATUSES PERFORMING THE SAME

(71) Applicant: Samsung Electronics Co., Ltd., Suwon-si, Gyeonggi-do (KR)

(72) Inventors: Byung-Kwon Choi, Suwon-si (KR); Tae Sin Ha, Seongnam-si (KR); Kee Hong Seo, Seoul (KR); Chang Hyun Roh, Seoul (KR); Young Bo Shim, Seoul (KR); Joon-Kee Cho, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 80 days.

(21) Appl. No.: 14/953,620

(22) Filed: Nov. 30, 2015

(65) Prior Publication Data

US 2017/0027801 A1  Feb. 2, 2017

(30) Foreign Application Priority Data

Jul. 27, 2015  (KR) .................. 10-2015-0105994

(51) Int. Cl.
*A63B 24/00* (2006.01)
*A61H 3/00* (2006.01)
(Continued)

(52) U.S. Cl.
CPC .............. *A61H 3/00* (2013.01); *A61B 5/0205* (2013.01); *A61B 5/112* (2013.01);
(Continued)

(58) Field of Classification Search
CPC ................ A63B 24/00; A63B 24/0067; A63B 24/0082; A63B 23/04; A63B 23/0087; A61H 3/00; A61H 3/008; A61H 3/024; A61H 2201/165; A61H 2201/5058; A61B 5/0205; A61B 5/112; A61B 5/14546; A61B 5/14542; A61B 5/4266; A61B 5/0816

See application file for complete search history.

(56) References Cited

U.S. PATENT DOCUMENTS 7,153,242 B2 * 12/2006 Goffer .................. A61F 5/0102
482/66
7,880,552 B2  2/2011 Yasuhara et al.
(Continued)

FOREIGN PATENT DOCUMENTS

JP  5075783 B2  11/2012
JP  5189911 B2   4/2013
(Continued)

*Primary Examiner* — Glenn Richman
(74) *Attorney, Agent, or Firm* — Harness, Dickey & Pierce, P.L.C.

(57) ABSTRACT

A walking assistance method may include: computing an amount of exercise of a user based on a biosignal of the user; adjusting a pattern of an assist parameter based on the amount of exercise; and/or generating a force corresponding to the amount of exercise, based on the adjusted pattern. A walking assistance apparatus may include: a pattern adjuster configured to compute an amount of exercise of a user based on a biosignal of the user; and/or a driver configured to generate a force corresponding to the amount of exercise based on a pattern of an assist parameter based on the amount of exercise.

18 Claims, 10 Drawing Sheets

(51) Int. Cl.

| | |
|---|---|
| *A63B 23/04* | (2006.01) |
| *A61B 5/0205* | (2006.01) |
| *A61B 5/11* | (2006.01) |
| *A61B 5/145* | (2006.01) |
| *A61B 5/00* | (2006.01) |
| *A61B 5/08* | (2006.01) |

(52) U.S. Cl.
 CPC ...... *A61B 5/14542* (2013.01); *A61B 5/14546* (2013.01); *A61B 5/4266* (2013.01); *A63B 23/04* (2013.01); *A63B 24/0087* (2013.01); *A61B 5/0816* (2013.01); *A61H 2201/165* (2013.01); *A61H 2201/5058* (2013.01)

(56) References Cited

U.S. PATENT DOCUMENTS

| | | | |
|---|---|---|---|
| 8,551,027 | B2 | 10/2013 | Endo et al. |
| 8,690,802 | B2 | 4/2014 | Sankai |
| 9,216,131 | B2 * | 12/2015 | Nakashima .............. A61H 3/00 |
| 9,314,622 | B2 * | 4/2016 | Embrey ............... A61N 1/36003 |
| 9,351,900 | B2 * | 5/2016 | Walsh ................... A61H 1/024 |
| 2012/0165704 | A1 | 6/2012 | Kang et al. |
| 2014/0163434 | A1 * | 6/2014 | Sankai .................. A61H 3/008 |
| | | | 601/23 |
| 2014/0276262 | A1 | 9/2014 | Kare et al. |
| 2017/0027801 | A1 * | 2/2017 | Choi ........................ A61H 3/00 |

FOREIGN PATENT DOCUMENTS

| | | |
|---|---|---|
| KR | 19990066566 A | 8/1999 |
| KR | 101033373 B1 | 5/2011 |
| KR | 101203669 B1 | 11/2012 |
| KR | 101221046 B1 | 2/2013 |

* cited by examiner

100

WALKING ASSISTANCE METHODS AND APPARATUSES PERFORMING THE SAME

CROSS-REFERENCE TO RELATED APPLICATION(S)

This application claims priority from Korean Patent Application No. 10-2015-0105994, filed on Jul. 27, 2015, in the Korean Intellectual Property Office (KIPO), the entire contents of which are incorporated herein by reference.

BACKGROUND

1. Field

Some example embodiments may relate generally to walking assistance methods. Some example embodiments may relate generally to walking assistance apparatuses configured to perform the walking assistance methods.

2. Description of Related Art

With the onset of rapidly aging societies, many people may experience inconvenience and pain from joint problems, and interest in walking assistance apparatuses enabling the elderly or patients with joint problems to walk with less effort, may increase. Furthermore, walking assistance apparatuses for intensifying muscular strength of human bodies may be useful for military purposes.

The users may wear the motion assistance apparatuses over the users' clothing.

Although some example embodiments will be described with relation to walking assistance methods and walking assistance apparatuses for humans, those skilled in the art will appreciate that some example embodiments may be applied to other types of methods, apparatuses, and systems, such as motion assistance methods and motion assistance apparatuses for animals, or more general purpose systems.

SUMMARY

Some example embodiments may provide walking assistance methods.

Some example embodiments may provide walking assistance apparatuses.

Some example embodiments may provide walking assistance apparatuses configured to perform the walking assistance methods.

In some example embodiments, a walking assistance method may comprise: computing an amount of exercise of a user based on a biosignal of the user; adjusting a pattern of an assist parameter based on the amount of exercise; and/or generating a force corresponding to the amount of exercise, based on the adjusted pattern.

In some example embodiments, the biosignal may comprise at least one of a heart rate, a breathing speed, a blood oxygen concentration, a lactic acid concentration, or an amount of sweat.

In some example embodiments, the generating of the force may comprise changing a gait velocity or an assistance torque corresponding to the assist parameter, based on the adjusted pattern.

In some example embodiments, the adjusting of the pattern may comprise adjusting at least one of an amplitude of a peak in the pattern, a position of the peak, an interval length of the peak, or an interval length of a base of the pattern.

In some example embodiments, the computing of the amount of exercise may comprise: receiving user information of the user; and/or computing the amount of exercise based on the user information and the biosignal.

In some example embodiments, the user information may comprise at least one of an age of the user, a stable-state heart rate of the user, or a gait intensity.

In some example embodiments, the computing of the amount of exercise may comprise: computing at least one of a first heart rate corresponding to an age of the user or a second heart rate based on a gait intensity; and/or comparing the at least one of the first heart rate or the second heart rate to a heart rate of the user included in the biosignal to compute the amount of exercise.

In some example embodiments, the first heart rate may be a maximum heart rate corresponding to the age of the user. The second heart rate may comprise at least one of a minimum heart rate or a maximum heart rate based on the gait intensity.

In some example embodiments, the biosignal may be received from a walking assistance apparatus or an external apparatus of the walking assistance apparatus.

In some example embodiments, the external apparatus may be at least one of a remote controller configured to control the walking assistance apparatus or an electronic apparatus including a sensor configured to generate the biosignal.

In some example embodiments, a walking assistance apparatus may comprise: a pattern adjuster configured to compute an amount of exercise of a user based on a biosignal of the user; and/or a driver configured to generate a force corresponding to the amount of exercise based on a pattern of an assist parameter based on the amount of exercise.

In some example embodiments, the biosignal may comprise at least one of a heart rate, a breathing speed, a blood oxygen concentration, a lactic acid concentration, or an amount of sweat.

In some example embodiments, the driver may be further configured to change a gait velocity or an assistance torque corresponding to the assist parameter, based on the adjusted pattern.

In some example embodiments, the pattern adjuster may be further configured to adjust at least one of an amplitude of a peak of the pattern, a position of the peak, an interval length of the peak, or an interval length of a base of the pattern.

In some example embodiments, the pattern adjuster may be further configured to receive user information of the user. The pattern adjuster may be further configured to compute the amount of exercise based on the user information and the biosignal.

In some example embodiments, the user information may comprise at least one of an age of the user, a stable-state heart rate of the user, or a gait intensity.

In some example embodiments, the pattern adjuster may be further configured to compute at least one of a first heart rate corresponding to an age of the user or a second heart rate based on a gait intensity. The pattern adjuster may be further configured to compare the at least one of the first heart rate or the second heart rate to a heart rate of the user included in the biosignal to compute the amount of exercise.

In some example embodiments, the first heart rate may be a maximum heart rate corresponding to the age of the user. The second heart rate may comprise at least one of a minimum heart rate or a maximum heart rate based on the gait intensity.

In some example embodiments, the biosignal may be received from the walking assistance apparatus or an external apparatus of the walking assistance apparatus.

In some example embodiments, the external apparatus may be at least one of a remote controller configured to control the walking assistance apparatus or an electronic apparatus including a sensor configured to generate the biosignal.

BRIEF DESCRIPTION OF THE DRAWINGS

The above and/or other aspects and advantages will become more apparent and more readily appreciated from the following detailed description of example embodiments, taken in conjunction with the accompanying drawings, in which.

DETAILED DESCRIPTION

Figure 1:
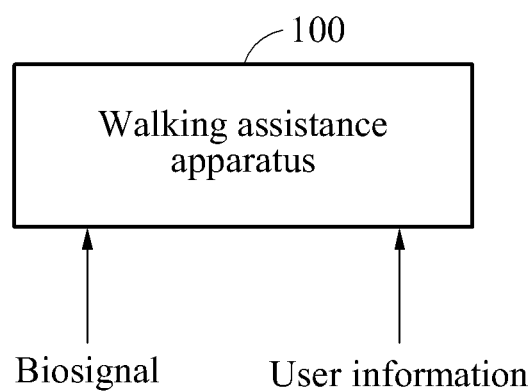
FIG. 1 is a block diagram illustrating an example of a walking assistance system according to some example embodiments.

Example embodiments will now be described more fully with reference to the accompanying drawings. Embodiments, however, may be embodied in many different forms and should not be construed as being limited to the embodiments set forth herein. Rather, these example embodiments are provided so that this disclosure will be thorough and complete, and will fully convey the scope to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Example embodiments may be described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will typically have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature, their shapes are not intended to illustrate the actual shape of a region of a device, and their shapes are not intended to limit the scope of the example embodiments.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, which are illustrated in the accompanying drawings, wherein like reference numerals may refer to like components throughout.

FIG. 1 is a block diagram illustrating an example of a walking assistance system according to some example embodiments.

Referring to FIG. 1, the walking assistance apparatus 100 may be worn by a target body, for example, a user, to assist a gait and/or a motion of the user. The target of object may be, for example, a person, an animal, or a robot, and examples of the target body is not limited thereto.

The walking assistance apparatus 100 may assist a gait and/or a motion of, for example, a hand, an upper arm, a lower arm, and or another part of an upper body of the user. Alternatively, the walking assistance apparatus 100 may assist a gait and/or a motion of, for example, a foot, a calf, a thigh, and or another part of a lower body of the user. Thus, the walking assistance apparatus 100 may assist a gait and/or a motion of a part of the user.

The walking assistance apparatus 100 may generate a force corresponding to an amount of exercise of a user based on a biosignal. As an example, the walking assistance apparatus 100 may change an assistance torque, for example, a torque intensity, and/or a gait velocity of the walking assistance apparatus 100 based on the amount of exercise of the user. The walking assistance apparatus 100 may sense the biosignal from the user.

In an example, the biosignal may include information on at least one of a heart rate, a breathing speed, a blood oxygen concentration, a lactic acid concentration, or an amount of sweat.

In another example, the biosignal may indicate any type of signal measured, monitored, or sensed from a biological being based on a continual, intermittent, or one-time method, and may be unique for each biological being. The biosignal may include, for example, an electrocardiogram (ECG) signal, a photoplethysmogram (PPG) signal, an electromyogram (EMG) signal, a voice, or an impedance signal generated in a body.

Also, the walking assistance apparatus 100 may generate a force corresponding to the amount of exercise of the user based on the biosignal and user information. For example, the walking assistance apparatus 100 may change the assistance torque and/or the gait velocity based on the amount of exercise of the user. The user information may include at least one of, for example, an age of the user, a stable-state heart rate of the user, or a gait intensity set in the walking assistance apparatus 100. The walking assistance apparatus 100 may directly receive the user information from the user.

Figure 2:
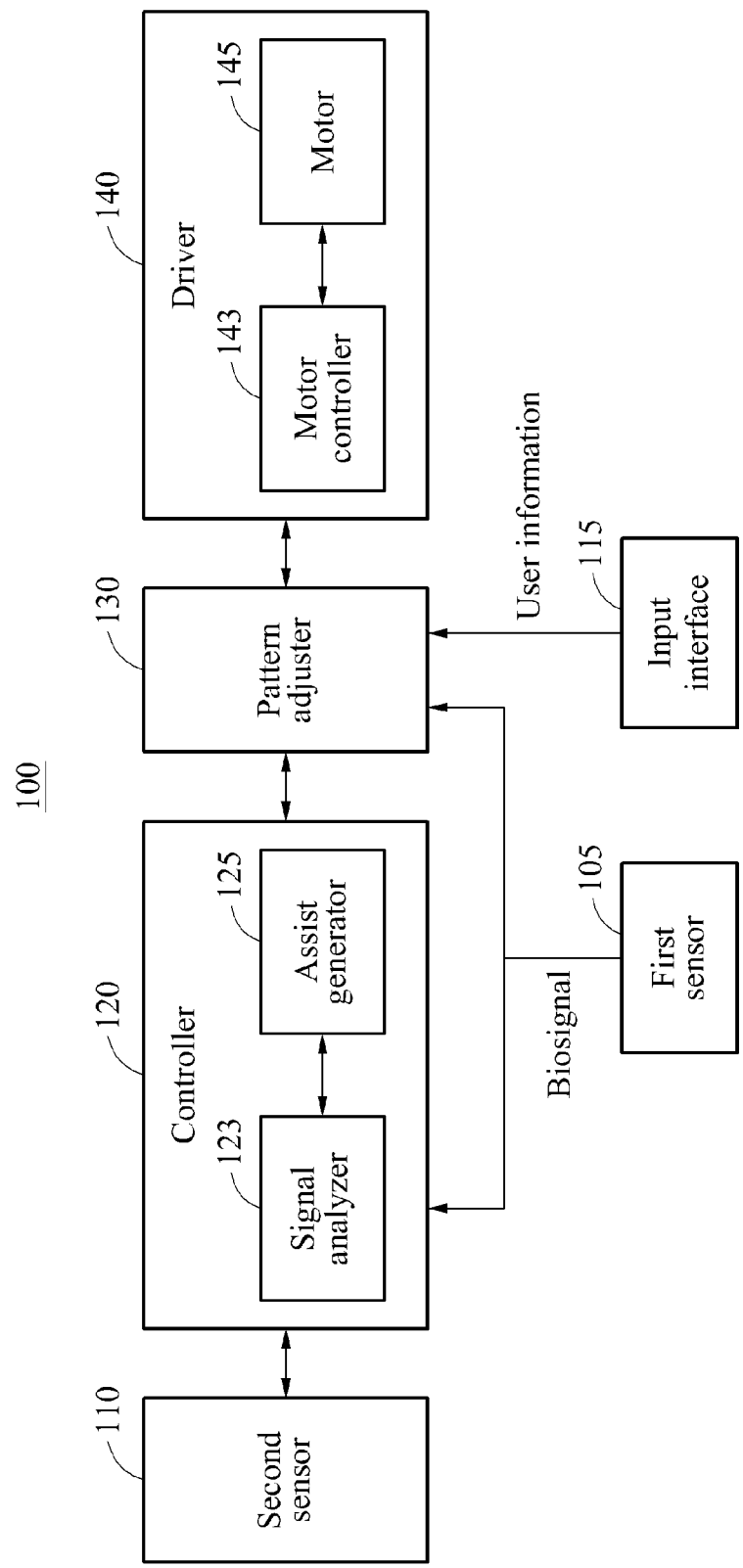
FIG. 2 is a block diagram illustrating a walking assistance apparatus of FIG. 1.
Figure 3:
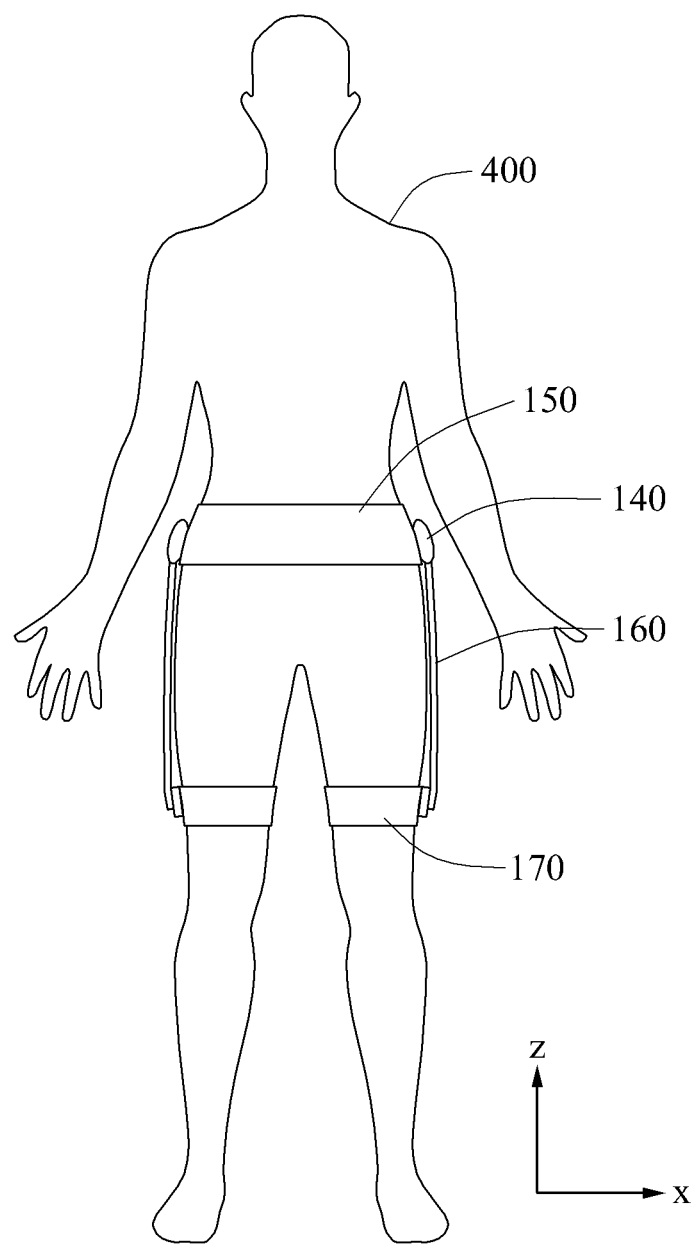
FIG. 3 is a front view illustrating a target body wearing the walking assistance apparatus of FIG. 1.
Figure 4:
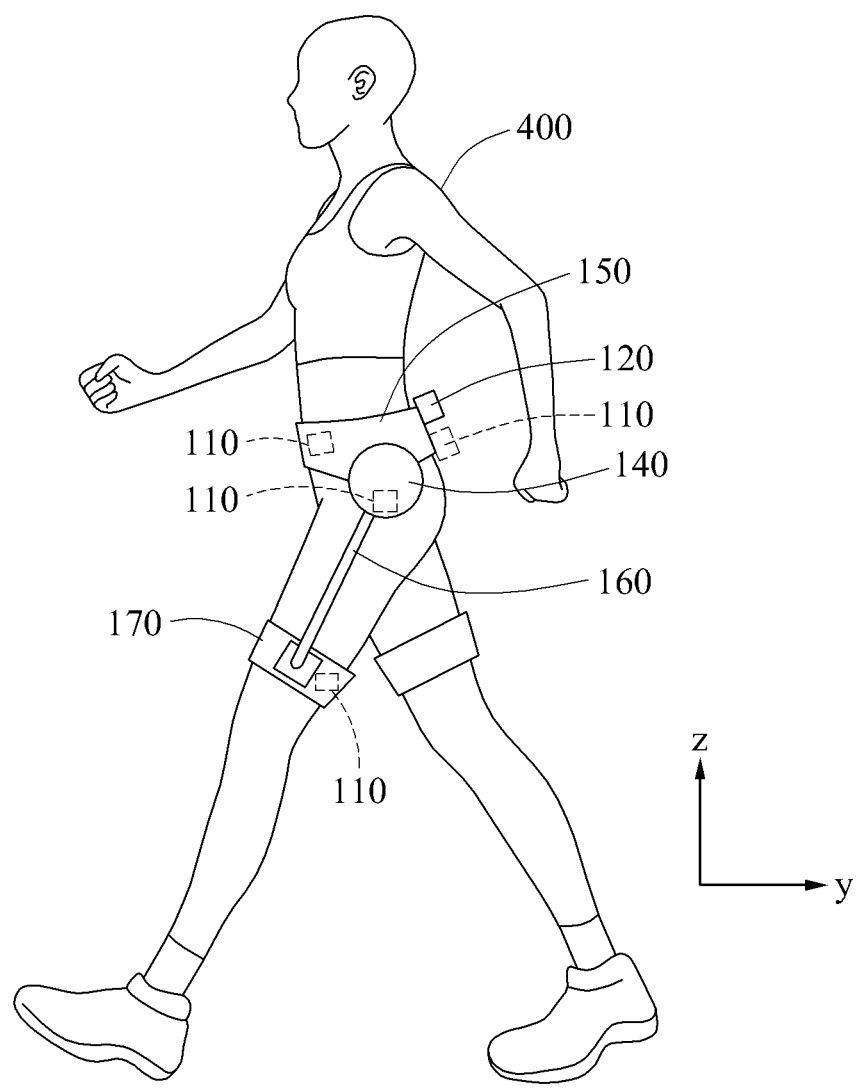
FIG. 4 is a side view illustrating a target body wearing the walking assistance apparatus of FIG. 1.

FIG. 2 is a block diagram illustrating a walking assistance apparatus of FIG. 1. FIG. 3 is a front view illustrating a target body wearing the walking assistance apparatus of FIG. 1. FIG. 4 is a side view illustrating a target body wearing the walking assistance apparatus of FIG. 1.

Although FIGS. 3 and 4 illustrate the walking assistance apparatus 100 as, for example, a hip-type walking assistance apparatus, operating on a thigh of the user, the type of the walking assistance apparatus 100 is not limited thereto. The walking assistance apparatus 100 may assist a motion of another part of an upper body, for example, a hand, an upper arm, or a lower arm of the user, or a motion of another part of a lower body, for example, a foot or a calf of the user. The walking assistance apparatus 100 may be applicable to, for example, a walking assistance apparatus that supports an entire pelvic limb, a walking assistance apparatus that supports a portion of a pelvic limb, etc. The walking assistance apparatus that supports a portion of a pelvic limb may be applicable to, for example, a walking assistance apparatus that supports up to a knee, or a walking assistance apparatus that supports up to an ankle.

In some example embodiments, a motion assistance apparatus for a robot could establish a master/slave or slave/master relationship between the motion assistance apparatus and robot. Such a master device may not be a single device, but may include more than one device, each performing one or more functions of the master device (e.g., the functionality of the master device may be distributed). Similarly, the slave device may not be a single device, but may include more than one device, each performing one or more functions of the slave device (e.g., the functionality of the slave device may be distributed). Therefore, the functionality of the master device, the slave device, or the master and slave devices may be distributed.

In some example embodiments, in such master/slave or slave/master relationship, the master device may be required to perform certain functions, but may or may not perform other functions while maintaining its role as the master device. One or more of these other functions may be shared with or performed by the slave device (which maintains its role as the slave device). Similarly, the slave device may be required to perform certain functions, but may or may not perform other functions while maintaining its role as the slave device. One or more of those other functions may be shared with or performed by the master device (which maintains its role as the master device). Thus, the required functionality of the master and slave devices may be maintained, while functionality that may be shared with or performed by the other device may be so shared with or performed by the other device consistent with the master device maintaining its role as the master device and the slave device maintaining its role as the slave device.

Although FIG. 3 illustrates a case in which the walking assistance apparatus 100 is a two-sided embodiment, in some example embodiments, the walking assistance apparatus 100 may be a one-sided embodiment.

Although FIG. 3 illustrates a case in which the motion assistance apparatus 10 may assist a motion of both thighs of the user, in some example embodiments, the walking assistance apparatus 100 may also assist a motion of only one thigh of a user at a time.

Referring to FIGS. 1 through 4, the walking assistance apparatus 100 may include a first sensor 105, a second sensor 110, an input interface 115, a controller 120, a pattern adjuster 130, and a driver 140. Also, the walking assistance apparatus 100 may further include a fixing member 150, a force transmitting member 160, and a supporting member 170.

The first sensor 105 may sense a biosignal of a user wearing the walking assistance apparatus 100. The first sensor 105 may be, for example, a biometric sensor. The first sensor 105 may transmit the biosignal to the controller 120 and the pattern adjuster 130.

The second sensor 110 may measure motion information of a user 400 while the user 400 is walking. As illustrated in FIG. 4, the second sensor 110 may be implemented in the driver 140, the fixing member 150, and the supporting member 170. Alternatively, the second sensor 110 may be implemented or mounted on a waist to which the fixing member 150 is attached. Depending on an example, the second sensor 110 may also be implemented or mounted, for example, on a shin, a thigh, or an ankle.

As an example, the second sensor 110 may measure hip joint angular information of both hips of the user 400 while the user 400 is walking. For example, the hip joint angular information may include at least one of angles of both hip joints, a difference in the angles of the hip joints, moving directions of the hip joints, or angular velocity information of the hip joints.

As another example, the second sensor 110 may sense acceleration information and posture information while the user 400 is walking. For example, the second sensor 110 may sense at least one of x-axial, y-axial, and z-axial accelerations or x-axial, y-axial, and z-axial angular velocities. The second sensor 110 may be, for example, an inertial measurement unit (IMU) sensor.

Thus, the motion information may include at least one of the hip joint angular information for both hips, the acceleration information, and the posture information.

The second sensor 110 may transmit the measured motion information to the controller 120.

The input interface 115 may receive user information from the user 400. Thus, the user 400 may input the user information through the input interface 115.

In an example, the input interface 115 may include a display (not shown). The display may be implemented as, for example, a touch screen, a liquid crystal display (LCD), a thin film transistor-liquid crystal display (TFT-LCD), a light emitting diode (LED) display, an organic LED (OLED) display, an active matrix OLED (AMOLED) display, and a flexible display.

The input interface 115 may provide a user interface (UI) and/or a menu corresponding to a function to manipulate the walking assistance apparatus 100 to the user 400 through the display.

The input interface 115 may display an operation status of the walking assistance apparatus 100 to be viewed by the user 400 on the display under control of the controller 120.

The input interface 115 may transmit the user information received from the user 400 to the pattern adjuster 130.

The controller 120 may control an overall operation of the walking assistance apparatus 100. For example, the controller 120 may control the driver 140 to output a force for assisting a gait of the user 400. The force may include at least one of an assistance torque and a gait velocity.

As an example, the controller 120 may control the driver 140 to output the force for assisting the gait of the user 400 based on the motion information transmitted from the second sensor 110.

As another example, the controller 120 may control the driver 140 to output the force for assisting the gait of the user 400 based on the biosignal transmitted from the first sensor 105.

The controller 120 may include a signal analyzer 123 and an assist generator 125.

The signal analyzer 123 may analyze the motion information transmitted from the second sensor 110. Also, the signal analyzer 123 may analyze the biosignal transmitted from the first sensor 105.

The assist generator 125 may generate assist parameters corresponding to a gait cycle based on a signal analysis result of the signal analyzer 123. The assist parameters may include assist torque parameters, for example, a flexion peak torque, a flexion peak duration, a flexion ascending duration, a flexion descending duration, an extension peak location, an extension peak torque, an extension peak duration, an extension ascending duration, and an extension descending duration.

As an example, the assist generator 125 may generate assist parameters corresponding to a motion information analysis result. As another example, the assist generator 125 may generate assist parameters corresponding to a biosignal analysis result.

The assist generator 125 may transmit the assist parameters to the pattern adjuster 130.

The pattern adjuster 130 may compute an amount of exercise of the user 400 based on the biosignal transmitted from the first sensor 105. Also, the pattern adjuster 130 may receive user information from the input interface 115, and compute the amount of exercise of the user 400 based on the user information and the biosignal. The user information may include, for example, an age of the user 400, a stable-state heart rate of the user 400, and the gait intensity set for the walking assistance apparatus 100. Thus, the user 400 may input or set the age, the stable-state heart rate, and the gait intensity through the input interface 115. In terms of the stable-state heart rate, a stable-state heart rate may be automatically set based on an input age.

The pattern adjuster 130 may adjust at least one pattern of the assist parameters generated by the assist generator 125 based on the amount of exercise.

Figure 5:
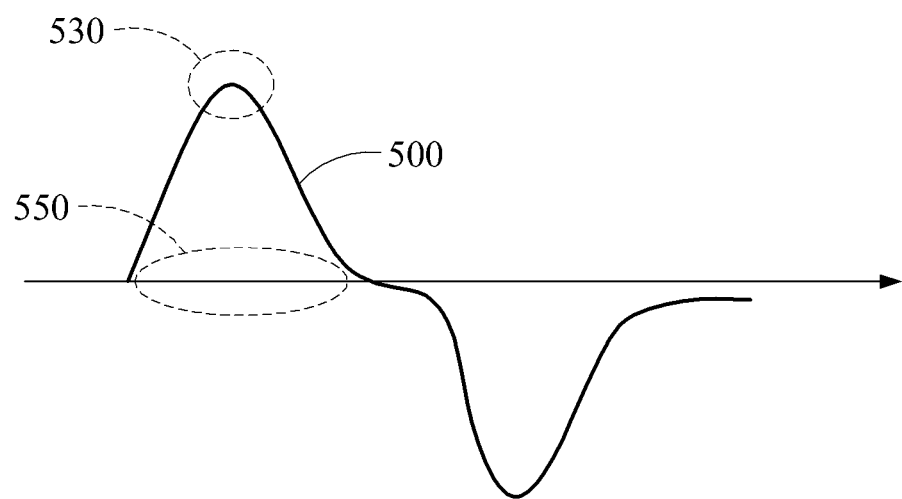
FIG. 5 illustrates an example of a pattern of an assist parameter according to some example embodiments.

Referring to FIG. 5, a pattern 500 may correspond to a gait cycle. For example, the pattern 500 may be expressed using a waveform to correspond to each point in time of the gait cycle. The pattern 500 may include a peak 530 and a base 550. The pattern adjuster 130 may adjust at least one of an amplitude of the peak 530 in the pattern 500, a position of the peak 530, an interval length of the peak 530, or an interval length of the base 550.

The pattern adjuster 130 may output the assist parameters having the adjusted pattern to the driver 140.

The driver 140 may be disposed on each of a left-hip portion and a right-hip portion of the user 400 to drive both hip joints of the user 400.

The driver 140 may generate a force corresponding to the amount of exercise of the user 400 based on the adjusted pattern. As an example, the driver 140 may change at least one of the gait velocity or an assistance torque, for example, a torque intensity, corresponding to at least one assist parameter based on the adjusted pattern. Thus, at least one of the gait velocity or the assistance torque of the walking assistance apparatus 100 may be changed when the driver 140 generates the force based on the adjusted pattern.

The driver 140 may include a motor controller 143 and a motor 145.

The motor controller 143 may generate a control signal to control the motor 145. Also, the motor controller 143 may generate the control signal to change at least one of the gait velocity or the assistance torque corresponding to the at least one assist parameter based on the adjusted pattern.

The motor 145 may generate a force in response to the control signal.

The fixing member 150 may be attached to a part, for example, a waist of the user 400. The fixing member 150 may be in contact with at least a portion of an external surface of the user 400. The fixing member 150 may cover along the external surface of the user 400.

The force transmitting member 160 may be disposed between the driver 140 and the supporting member 170 to connect the driver 140 and the supporting member 170. The force transmitting member 160 may transmit the force received from the driver 140 to the supporting member 170. As an example, the force transmitting member 160 may be a longitudinal member such as, for example, a wire, a cable, a string, a rubber band, a spring, a belt, or a chain.

The supporting member 170 may support a target part, for example, a thigh of the user 400. The supporting member 170 may be disposed to cover at least a portion of the user 400. The supporting member 170 may apply a force to the target part of the user 400 using the force received from the force transmitting member 160.

Figure 6:
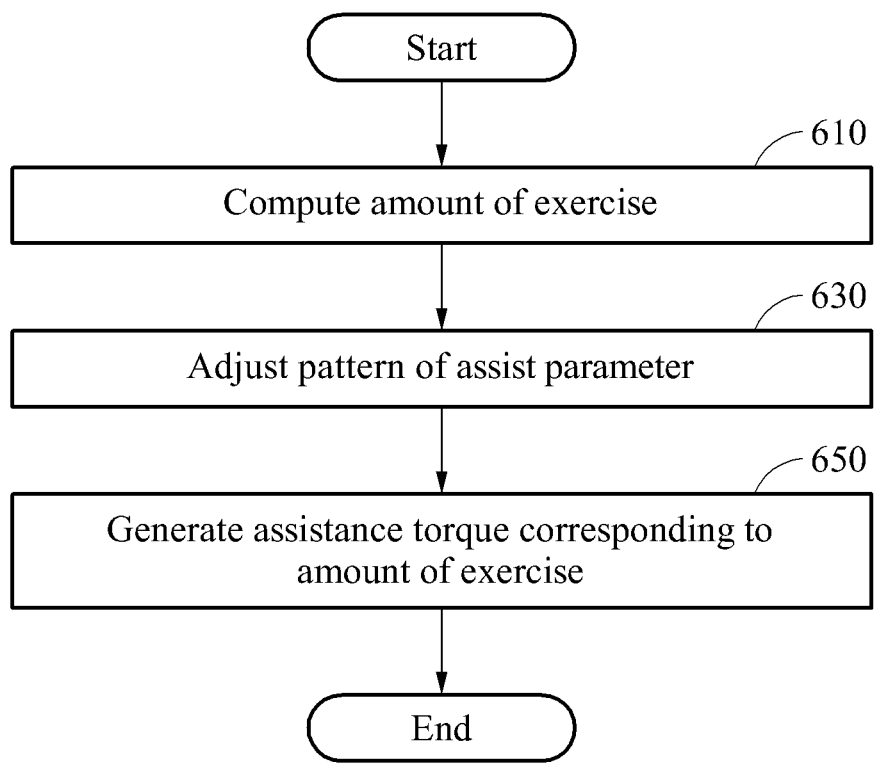
FIG. 6 is a flowchart illustrating an example of an operation method of the walking assistance apparatus in FIG. 1.

FIG. 6 is a flowchart illustrating an example of an operation method performed by the walking assistance apparatus 100 of FIG. 1.

Referring to FIGS. 1 through 6, in operation 610, the pattern adjuster 130 may compute an amount of exercise of the user 400 based on a biosignal transmitted from the first sensor 105. Also, the pattern adjuster 130 may receive user information from the input interface 115 and compute the amount of exercise of the user 400 based on the user information and the biosignal.

In operation 630, the pattern adjuster 130 may adjust at least one pattern of assist parameters generated by the assist generator 125 based on the amount of exercise.

In operation 650, the driver 140 may generate an assistance torque corresponding to the amount of exercise of the user 400 based on the adjusted pattern. For example, the driver 140 may change a gait velocity and the assistance torque corresponding to the at least one assist parameter based on the adjusted pattern.

Figure 7:
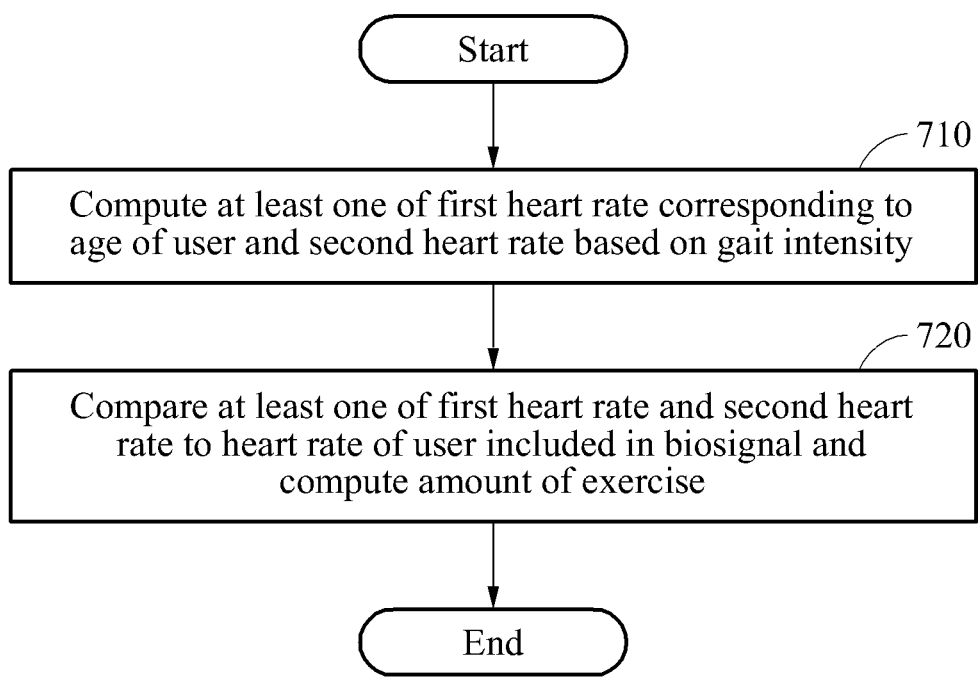
FIG. 7 is a flowchart illustrating an example of an exercise amount computation method performed by a pattern adjuster of FIG. 2.
Figure 8:
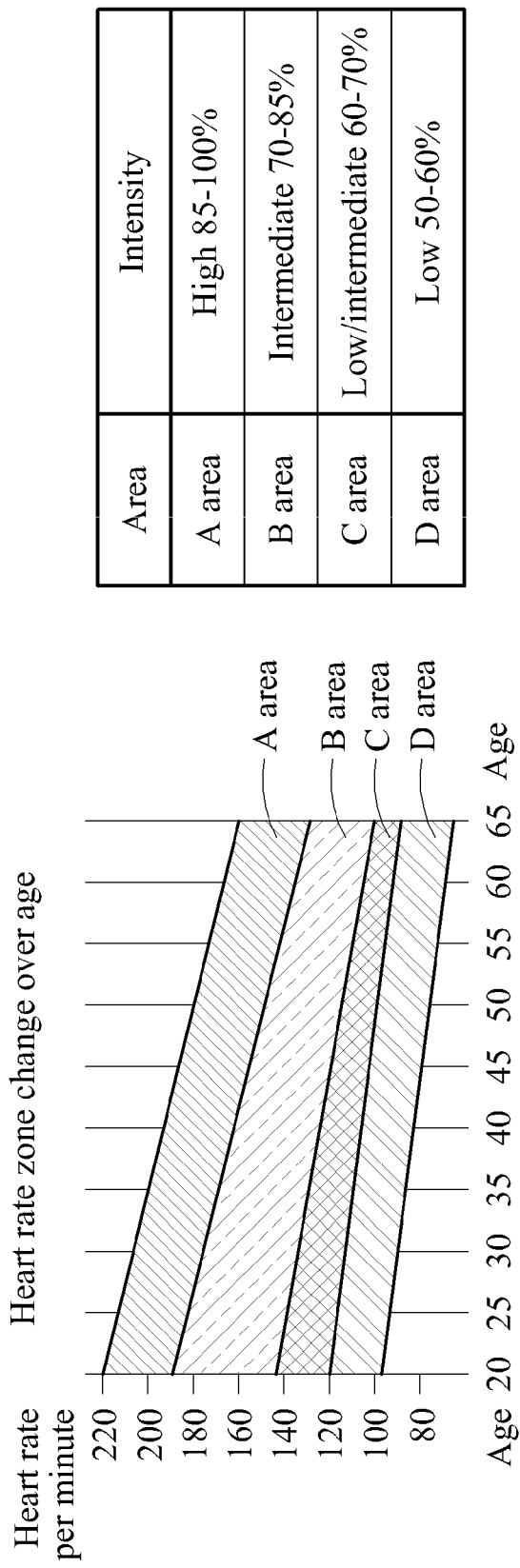
FIG. 8 is a flowchart illustrating an example of user information used in an exercise amount computation of a pattern adjuster according to some example embodiments.

FIG. 7 is a flowchart illustrating an example of an exercise amount computation method performed by the pattern adjuster 130 of FIG. 2. FIG. 8 is a flowchart illustrating an example of user information used in an exercise amount computation of a pattern adjuster according to some example embodiments.

Referring to FIGS. 7 and 8, the pattern adjuster 130 may receive user information from the input interface 115, and may compute an amount of exercise of the user 400 based on the user information and a biosignal.

For example, the biosignal may include information on at least one of a heart rate, a breathing speed, a blood oxygen concentration, a lactic acid concentration, or an amount of sweat. Hereinafter, for increased clarity and conciseness, descriptions will be provided based on an example in which the biosignal includes information on the heart rate.

In operation 710, the pattern adjuster 130 may compute at least one of a first heart rate corresponding to an age of the user 400 or a second heart rate based on a gait intensity set in the walking assistance apparatus 100. For example, the first heart rate may be a maximum heart rate corresponding to the age of the user 400, and the second heart rate may include at least one of a maximum heart rate and a minimum heart rate based on the gait intensity set in the walking assistance apparatus 100.

The pattern adjuster 130 may compute the first heart rate, for example, HeartRate_max_threshold, based on Equation 1. In this example, the user 400 may be assumed as a normal user, for example, a normal person.

$$\text{HeartRate\_max\_threshold(cycle/minute)}=220-\text{age} \quad \text{[Equation 1]}$$

The pattern adjuster 130 may compute the second heart rate, for example, HeartRate_exercise_intensity, based on Equation 2.

$$\text{HeartRate\_exercise\_intensity(cycle/minute)}=[(\text{maximum heart rate}-\text{stable-state heart rate})\times\text{gait intensity}]+\text{stable-state heart rate} \quad \text{[Equation 2]}$$

In Equation 2, the maximum heart rate may indicate the first heart rate computed through Equation 1, for example, the maximum heart rate corresponding to the age.

FIG. 8 illustrates an example of a gait intensity. An area A may indicate a high intensity exercise, for example, a professional training. An area B may indicate an intermediate intensity exercise, for example, a performance-enhancing exercise. An area C may indicate a low/intermediate intensity exercise, for example, a weight control exercise. An area D may indicate a low intensity exercise, for example, a light exercise. Thus, the gait intensity may indicate, for example, an exercise intensity.

As an example, a 60-year-old user may have a stable-state heart rate corresponding to 70 and set the gait intensity of the walking assistance apparatus 100 to a low intensity. In this example, the first heart rate may be computed as, for example, HeartRate_max_threshold=220−60=160. Also, the second heart rate may be computed as, for example, $$\text{HeartRate\_exercise\_intensity\_min}=(160-70)\times0.5+70=115 \text{ and}$$

$$\text{HeartRate\_exercise\_intensity\_max}=(160-70)\times0.6+70=124.$$

In operation 720, the pattern adjuster 130 may compare at least one of the first heart rate or the second heart rate to a heart rate of the user 400 included in the biosignal, thereby computing the amount of exercise of the user 400.

Hereinafter, descriptions related to a control operation of the walking assistance apparatus 100 based on the exercise amount computation method described with reference to FIGS. 7 and 8 will be provided as an example.

Figure 9:
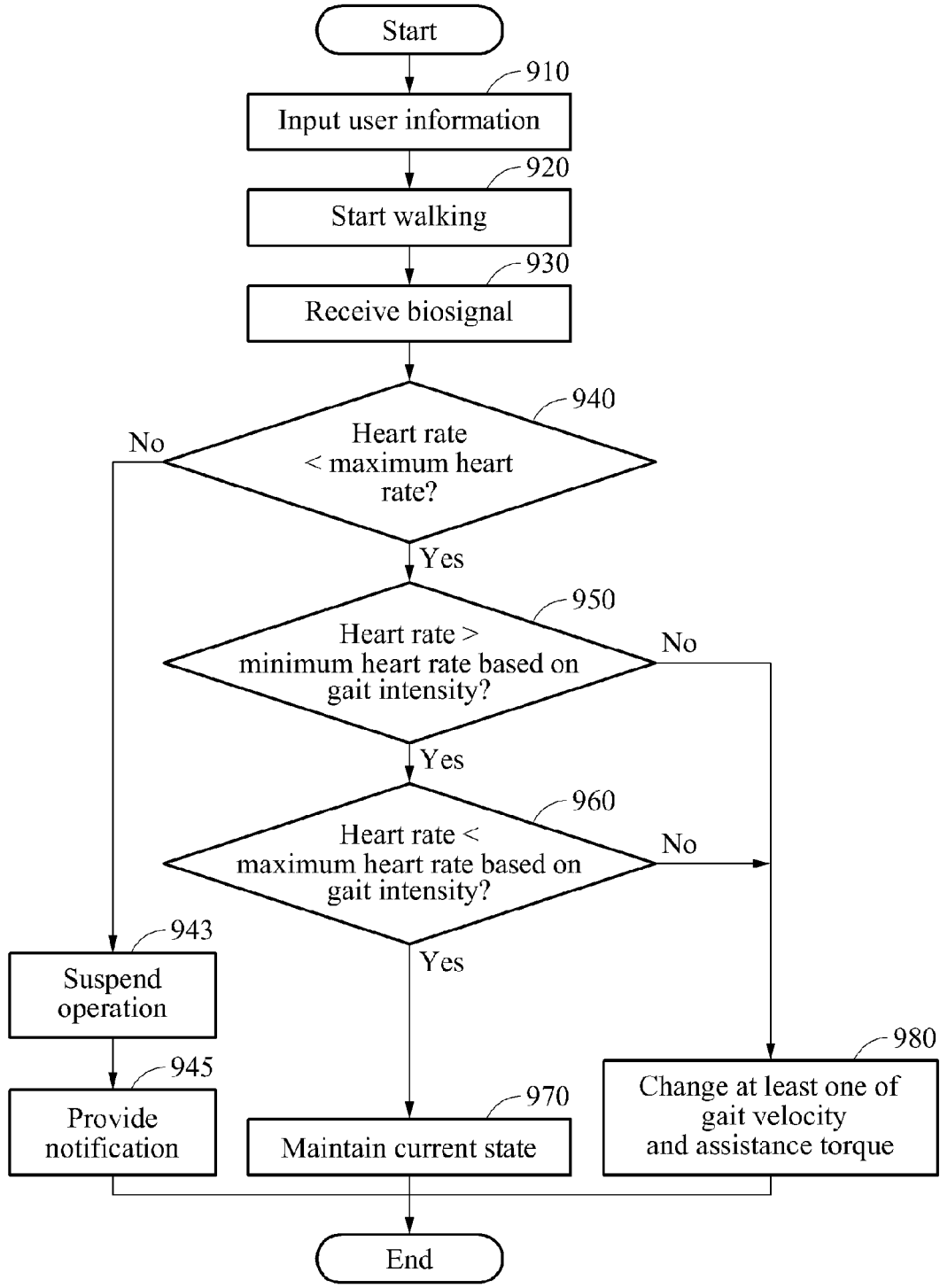
FIG. 9 is a flowchart illustrating an example of a control operation of a walking assistance apparatus according to some example embodiments.

FIG. 9 is a flowchart illustrating an example of a control operation of a walking assistance apparatus according to some example embodiments.

Referring to FIGS. 7 through 9, in operation 910, the user 400 may input user information through the input interface 115. For example, the user 400 may input an age, a stable-state heart rate, and a gait intensity through the input interface 115.

In operation 920, the user 400 may start walking using the walking assistance apparatus 100. For example, the controller 120 may control the driver 140 to output an assistance torque for assisting a gait of the user 400. In this example, the driver 140 may generate a force based on assist parameters corresponding to a gait cycle output from the controller 120.

In operation 930, the pattern adjuster 130 may receive a biosignal transmitted from the first sensor 105.

The pattern adjuster 130 may receive user information input through the input interface 115, and may compute an amount of exercise of the user 400 based on the user information and the biosignal.

In operation 940, the pattern adjuster 130 may compare a heart rate included in the biosignal to a maximum heart rate corresponding to the age of the user 400.

When the heart rate is greater than or equal to the maximum heart rate, the pattern adjuster 130 may determine that the amount of exercise of the user 400 is beyond a normal range and control the driver 140 to suspend an operation of the walking assistance apparatus 100 in operation 943. When the heart rate included in the biosignal is maintained to be abnormal after the operation of the walking assistance apparatus 100 is suspended, the pattern adjuster 130 may provide notification on an abnormality to the user 400 directly or by controlling an alarm device (not shown) included in the walking assistance apparatus 100 in operation 945.

When the heart rate is less than or equal to the maximum heart rate, the pattern adjuster 130 may compare the heart rate included in the biosignal to a minimum heart rate based on the gait intensity in operation 950.

When the heart rate is less than or equal to the minimum heart rate, the pattern adjuster 130 may adjust a pattern of an assist parameter and the driver 140 may change at least one of a gait velocity and an assistance torque of the walking assistance apparatus 100 based on the adjusted pattern in operation 980. As an example, the driver 140 may increase the gait velocity or decrease the assistance torque, for example, a torque intensity.

When the heart rate is greater than the minimum heart rate, the pattern adjuster 130 may compare the heart rate included in the biosignal to a maximum heart rate based on the gait intensity in operation 960.

When the heart rate is greater than or equal to the maximum heart rate based on the gait intensity, the pattern adjuster 130 may adjust the pattern of the assist parameter and the driver 140 may change at least one of the gait velocity and the assistance torque of the walking assistance apparatus 100 based on the adjusted pattern in operation 980. For example, the driver 140 may increase the torque intensity or decrease the gait velocity of the walking assistance apparatus 100.

When the heart rate is less than the maximum heart rate based on the gait intensity, the pattern adjuster 130 may not adjust the pattern of the assist parameter such that the walking assistance apparatus 100 maintains a current state, for example, at least one of the gait velocity and the assistance torque in operation 970.

Operations 930 through 980 may be repetitively performed after the user 400 starts walking.

The walking assistance apparatus 100 may perform a gait assistance based on a heart rate, for example, an amount of exercise, thereby preventing an accident, increasing a safety, and improving an exercise effect.

Figure 10:
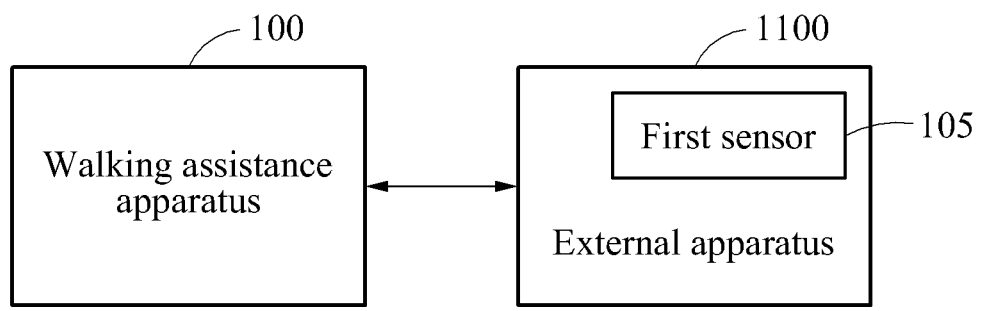
FIG. 10 is a block diagram illustrating another example of a walking assistance system according to some example embodiments.

FIG. 10 is a block diagram illustrating a walking assistance system 1000 according to some example embodiments.

Referring to FIG. 10, the walking assistance system 1000 may include the walking assistance apparatus 100 and an external apparatus 1100.

The first sensor 105 of the walking assistance apparatus 100 may be implemented in the external apparatus 1100. Through this, the walking assistance apparatus 100 may receive a biosignal sensed by the external apparatus 1100.

In an example, the external apparatus 1100 may be a controller, for example, a remote controller, configured to control an overall operation of the walking assistance apparatus 100.

The external apparatus 1100 may control the overall operation of the walking assistance apparatus 100 in response to a user input. For example, the external apparatus 1100 may initiate/suspend an operation of the walking assistance apparatus 100. The controller 120 of the walking assistance apparatus 100 may control the driver 140 to output a force for assisting a gait of the user 400 under control of the external apparatus 1100. Also, the external apparatus 1100 may control or change an assist parameter for controlling a force of the walking assistance apparatus 100.

The external apparatus 1100 may include a display (not shown). The display may be implemented as, for example, a touch screen, an LCD, a TFT-LCD, an LED display, an OLED display, an AMOLED display, and a flexible display.

The external apparatus 1100 may provide a UI and/or a menu corresponding to a function to manipulate the walking assistance apparatus 100 to a user through the display.

The display may display an operation status of the walking assistance apparatus 100 to be viewed by the user 400 under control of the external apparatus 1100.

In another example, the external apparatus 1100 may be, for example, an electronic device configured to mutually communicate with the walking assistance apparatus 100.

The electronic device may be implemented as, for example, a portable electronic device.

The portable electronic device may be implemented as, for example, a laptop computer, a mobile phone, a smartphone, a tablet personal computer (PC), a mobile internet device (MID), a personal digital assistant (PDA), an enterprise digital assistant (EDA), a digital still camera, a digital video camera, a portable multimedia player (PMP), a personal navigation device or portable navigation device (PND), a handheld game console, an e-book, or a smart device.

The smart device may be implemented as, for example, a smart watch or a smart band.

Also, the external apparatus 1100 may transmit user information of the user 400 to the walking assistance apparatus 100. The user may input the user information through the external apparatus 1100.

The algorithms discussed in this application (e.g., for walking assistance methods and apparatuses) may be used in more general purpose methods and/or apparatuses. For example, the algorithms may be used for more general methods and apparatuses.

The methods described above may be written as computer programs and can be implemented in general-use digital computers that execute the programs using a computer-readable recording medium. In addition, a structure of data used in the methods may be recorded in a computer-readable recording medium in various ways. Examples of the computer-readable recording medium include storage media such as magnetic storage media (e.g., ROM (Read-Only Memory), RAM (Random-Access Memory), USB (Universal Serial Bus), floppy disks, hard disks, etc.) and optical recording media (e.g., CD-ROMs (Compact Disc Read-Only Memories) or DVDs (Digital Video Discs)).

In addition, some example embodiments may also be implemented through computer-readable code/instructions in/on a medium (e.g., a computer-readable medium) to control at least one processing element to implement some example embodiments. The medium may correspond to any medium/media permitting the storage and/or transmission of the computer-readable code.

The computer-readable code may be recorded/transferred on a medium in a variety of ways, with examples of the medium including recording media, such as magnetic storage media (e.g., ROM, floppy disks, hard disks, etc.) and optical recording media (e.g., CD-ROMs or DVDs), and transmission media such as Internet transmission media. Thus, the medium may be such a defined and measurable structure including or carrying a signal or information, such as a device carrying a bitstream according to some example embodiments. The media may also be a distributed network, so that the computer-readable code is stored/transferred and executed in a distributed fashion. Furthermore, the processing element could include a processor or a computer processor, and processing elements may be distributed and/or included in a single device.

In some example embodiments, some of the elements may be implemented as a 'module'. According to some example embodiments, 'module' may be interpreted as software-based components or hardware components, such as a field programmable gate array (FPGA) or an application specific integrated circuit (ASIC), and the module may perform certain functions. However, the module is not limited to software or hardware. The module may be configured so as to be placed in a storage medium which may perform addressing, or to execute one or more processors.

For example, modules may include components such as software components, object-oriented software components, class components, and task components, processes, functions, attributes, procedures, subroutines, segments of program code, drivers, firmware, microcodes, circuits, data, databases, data structures, tables, arrays, and variables. Functions provided from the components and the modules may be combined into a smaller number of components and modules, or be separated into additional components and modules. Moreover, the components and the modules may execute one or more central processing units (CPUs) in a device.

Some example embodiments may be implemented through a medium including computer-readable codes/instructions to control at least one processing element of the above-described embodiment, for example, a computer-readable medium. Such a medium may correspond to a medium/media that may store and/or transmit the computer-readable codes.

The computer-readable codes may be recorded in a medium or be transmitted over the Internet. For example, the medium may include a ROM, a RAM, a CD-ROM, a magnetic tape, a floppy disc, an optical recording medium, or a carrier wave such as data transmission over the Internet. Further, the medium may be a non-transitory computer-readable medium. Since the medium may be a distributed network, the computer-readable code may be stored, transmitted, and executed in a distributed manner. Further, for example, the processing element may include a processor or a computer processor, and be distributed and/or included in one device.

Although some example embodiments have been shown and described, it would be appreciated by those skilled in the art that changes may be made in these example embodiments without departing from the principles and spirit of the example embodiments, the scope of which is defined in the claims and their equivalents. For example, while certain operations have been described as being performed by a given element, those skilled in the art will appreciate that the operations may be divided between elements in various manners.

Although some example embodiments are described above with relation to muscular strength assisting methods and apparatuses, those skilled in the art will appreciate that some example embodiments may be applied to other types of methods and systems, such as methods and systems not used in the medical field (e.g., aerospace teleoperation systems, apparatuses for handling hazardous materials, patrol apparatuses, military apparatuses), humanoid apparatuses, or more general purpose control systems. Those skilled in the art will appreciate that the muscular strength assisting methods and apparatuses described in this patent application have a myriad of practical uses.

Although some example embodiments of the present disclosure have been shown and described, it would be appreciated by those skilled in the art that changes may be made in these example embodiments without departing from the principles and spirit of the invention, the scope of which is defined in the claims and their equivalents.

It should be understood that the example embodiments described herein should be considered in a descriptive sense only and not for purposes of limitation. Descriptions of features or aspects within each embodiment should typically be considered as available for other similar features or aspects in other embodiments.

What is claimed is:

1. A walking assistance method, comprising:
   computing an amount of exercise of a user based on a biosignal of the user;
   adjusting a pattern of an assist parameter based on the amount of exercise to generate an adjusted pattern, the adjusting of the pattern including adjusting at least one of an amplitude of a peak in the pattern, a position of the peak, an interval length of the peak, or an interval length of a base of the pattern; and
   generating a force corresponding to the amount of exercise, based on the adjusted pattern.

2. The walking assistance method of claim 1, wherein the biosignal comprises at least one of a heart rate, a breathing speed, a blood oxygen concentration, a lactic acid concentration, or an amount of sweat.

3. The walking assistance method of claim 1, wherein the generating of the force comprises changing a gait velocity or an assistance torque corresponding to the assist parameter, based on the adjusted pattern.

4. The walking assistance method of claim 1, wherein the computing of the amount of exercise comprises:
   receiving user information of the user; and
   computing the amount of exercise based on the user information and the biosignal.

5. The walking assistance method of claim 4, wherein the user information comprises at least one of an age of the user, a stable-state heart rate of the user, or a gait intensity.

6. The walking assistance method of claim 1, wherein the computing of the amount of exercise comprises:
   computing at least one of a first heart rate corresponding to an age of the user or a second heart rate based on a gait intensity; and
   comparing the at least one of the first heart rate or the second heart rate to a heart rate of the user included in the biosignal to compute the amount of exercise.

7. The walking assistance method of claim 6, wherein the first heart rate is a maximum heart rate corresponding to the age of the user, and
   wherein the second heart rate comprises at least one of a minimum heart rate or a maximum heart rate based on the gait intensity.

8. The walking assistance method of claim 1, wherein the biosignal is received from a walking assistance apparatus or an external apparatus of the walking assistance apparatus.

9. The walking assistance method of claim 8, wherein the external apparatus is at least one of a remote controller configured to control the walking assistance apparatus or an electronic apparatus including a sensor configured to generate the biosignal.

10. A walking assistance apparatus, comprising:
    a pattern adjuster configured to,
       compute an amount of exercise of a user based on a biosignal of the user, and
       adjust at least one of an amplitude of a peak of a pattern of an assist parameter, a position of the peak, an interval length of the peak, or an interval length of a base of the pattern; and
    a driver configured to generate a force corresponding to the amount of exercise, based on the pattern adjusted by the pattern adjuster.

11. The walking assistance apparatus of claim 10, wherein the biosignal comprises at least one of a heart rate, a breathing speed, a blood oxygen concentration, a lactic acid concentration, or an amount of sweat.

12. The walking assistance apparatus of claim 10, wherein the driver is further configured to change a gait velocity or an assistance torque corresponding to the assist parameter, based on the adjusted pattern.

13. The walking assistance apparatus of claim 10, wherein the pattern adjuster is further configured to receive user information of the user, and
    wherein the pattern adjuster is further configured to compute the amount of exercise based on the user information and the biosignal.

14. The walking assistance apparatus of claim 13, wherein the user information comprises at least one of an age of the user, a stable-state heart rate of the user, or a gait intensity.

15. The walking assistance apparatus of claim 10, wherein the pattern adjuster is further configured to compute at least one of a first heart rate corresponding to an age of the user or a second heart rate based on a gait intensity, and
    wherein the pattern adjuster is further configured to compare the at least one of the first heart rate or the second heart rate to a heart rate of the user included in the biosignal to compute the amount of exercise.

16. The walking assistance apparatus of claim 15, wherein the first heart rate is a maximum heart rate corresponding to the age of the user, and
    wherein the second heart rate comprises at least one of a minimum heart rate or a maximum heart rate based on the gait intensity.

17. The walking assistance apparatus of claim 10, wherein the biosignal is received from the walking assistance apparatus or an external apparatus of the walking assistance apparatus.

18. The walking assistance apparatus of claim 17, wherein the external apparatus is at least one of a remote controller configured to control the walking assistance apparatus or an electronic apparatus including a sensor configured to generate the biosignal.

* * * * *